United States Patent
Gadsby (10) Patent No.: US 9,814,402 B2
(45) Date of Patent: Nov. 14, 2017

(54) ELECTRODE SYSTEMS FOR USE WITH MEDICAL MONITORING SYSTEMS

(71) Applicant: Acacia Designs BV, Maastricht (NL)

(72) Inventor: Peter Donald Gadsby, Broomfield, CO (US)

(73) Assignee: Acacia Designs BV, Maastricht (NL)

( * ) Notice: Subject to any disclaimer, the term of this patent is extended or adjusted under 35 U.S.C. 154(b) by 0 days.

(21) Appl. No.: 14/180,757

(22) Filed: Feb. 14, 2014

(65) Prior Publication Data

US 2014/0235991 A1    Aug. 21, 2014

Related U.S. Application Data

(60) Provisional application No. 61/765,355, filed on Feb. 15, 2013.

(51) Int. Cl.
*A61B 5/04* (2006.01)
*A61B 5/0492* (2006.01)

(52) U.S. Cl.
CPC ........ *A61B 5/04001* (2013.01); *A61B 5/0492* (2013.01); *A61B 2562/0209* (2013.01); *Y10T 29/49147* (2015.01)

(58) Field of Classification Search
CPC .......................... A61B 5/0492; A61B 5/04001
USPC .......................... 600/391–393, 546, 547, 554
See application file for complete search history.

(56) References Cited

U.S. PATENT DOCUMENTS

| | | |
|---|---|---|
| 3,364,929 A | 1/1968 | Ide et al. |
| 3,565,080 A | 2/1971 | Ide |
| 3,898,983 A | 8/1975 | Elam |
| 4,157,087 A | 6/1979 | Miller et al. |
| 4,291,705 A | 9/1981 | Severinghaus et al. |
| 4,387,723 A | 6/1983 | Atlee, III et al. |
| 4,570,640 A | 2/1986 | Barsa |
| 4,595,018 A | 6/1986 | Rantala |

(Continued)

OTHER PUBLICATIONS

Brull, S., et al., "Correlation of Train-of-Four and Double Burst Stimulation Ratios at Varying Amperages," Anesth Analg, vol. 71, 1990, pp. 489-492.
Brull, S., et al., "Stimulation with Submaximal Current for Train-of-Four Monitoring," Anesthesiology, vol. 72, 1990, pp. 629-632.
Carter, J.A., et al., "Assessment of the Datex Relaxograph during anaesthesia and atracurium-induced neuromuscular blockade," British Journal of Anaesthesia, vol. 58, No. 12, 1986, pp. 1447-1452.
Datex-Ohmeda Appliguide, Neuromuscular monitoring, 1998, 52 pages.

(Continued)

*Primary Examiner* — Lee S Cohen
(74) *Attorney, Agent, or Firm* — Meunier Carlin & Curfman LLC (57) ABSTRACT

Electrode systems for use with neuromuscular monitoring systems are provided herein. An example electrode system for use with a monitoring system can include a flexible substrate, a connector interface, one or more stimulating electrodes, one or more recording electrodes and a plurality of conductive traces carried on the flexible substrate. The connector interface can be configured to communicatively connect the electrode system with the monitoring system. In addition, the one or more stimulating electrodes can be configured to deliver an electrical pulse, and the one or more recording electrodes can be configured to receive an electrical signal. The plurality of conductive traces can electrically connect at least one stimulating electrode or at least one recording electrode with the connector interface. Further, each of the one or more stimulating electrodes can have an elongate shape with a length dimension that is substantially greater than a width dimension.

43 Claims, 4 Drawing Sheets

(56) References Cited

U.S. PATENT DOCUMENTS

| | | | |
|---|---|---|---|
| 4,817,628 A | 4/1989 | Zealear et al. | |
| 5,131,401 A | 7/1992 | Westenskow et al. | |
| 5,300,096 A | 4/1994 | Hall et al. | |
| 5,327,902 A | 7/1994 | Lemmen | |
| 5,391,081 A | 2/1995 | Lampotang et al. | |
| 5,851,191 A | 12/1998 | Gozani | |
| 5,957,860 A | 9/1999 | Rodiera Olive | |
| 5,976,094 A | 11/1999 | Gozani | |
| 6,002,960 A | 12/1999 | Sternberger et al. | |
| 6,076,011 A | 6/2000 | Hoover | |
| 6,132,387 A | 10/2000 | Gozani et al. | |
| 6,146,335 A | 11/2000 | Gozani | |
| 6,379,313 B1 | 4/2002 | Gozani et al. | |
| 6,385,473 B1* | 5/2002 | Haines | A61B 5/04085 600/382 |
| 6,389,312 B1 | 5/2002 | Duckert | |
| 6,500,128 B2 | 12/2002 | Marino | |
| 6,654,626 B2* | 11/2003 | Devlin | A61B 5/04085 600/372 |
| 6,692,444 B2 | 2/2004 | Gozani et al. | |
| 6,896,661 B2 | 5/2005 | Dekker | |
| 6,975,901 B2 | 12/2005 | Philip | |
| 7,130,673 B2* | 10/2006 | Tolvanen-Laakso | A61B 5/0478 600/383 |
| 7,169,125 B2 | 1/2007 | Jansen et al. | |
| 7,236,832 B2 | 6/2007 | Hemmerling et al. | |
| 7,452,335 B2 | 11/2008 | Wells et al. | |
| 7,558,610 B1 | 7/2009 | Odderson | |
| 7,628,761 B2 | 12/2009 | Gozani et al. | |
| 7,925,338 B2 | 4/2011 | Huiku | |
| 8,078,273 B2 | 12/2011 | Krishnamachari et al. | |
| 8,229,872 B2 | 7/2012 | Gilhuly | |
| 8,577,440 B2* | 11/2013 | Afanasewicz | A61B 5/0478 600/383 |
| 2002/0123700 A1 | 9/2002 | Tung | |
| 2004/0015096 A1 | 1/2004 | Mok et al. | |
| 2004/0024299 A1 | 2/2004 | Grace et al. | |
| 2004/0122482 A1 | 6/2004 | Tung et al. | |
| 2004/0158170 A1 | 8/2004 | Overstreet et al. | |
| 2005/0277819 A1* | 12/2005 | Kiani | A61B 5/0478 600/324 |
| 2006/0111756 A1 | 5/2006 | Chang | |
| 2006/0270943 A1 | 11/2006 | Kamataki et al. | |
| 2007/0129771 A1 | 6/2007 | Kurtz et al. | |
| 2007/0270678 A1* | 11/2007 | Fadem | A61B 5/0006 600/372 |
| 2007/0270918 A1 | 11/2007 | De Bel et al. | |
| 2007/0282217 A1 | 12/2007 | McGinnis et al. | |
| 2007/0293782 A1 | 12/2007 | Marino | |
| 2009/0018610 A1 | 1/2009 | Gharib et al. | |
| 2009/0036792 A1 | 2/2009 | DeLuca et al. | |
| 2010/0081963 A1 | 4/2010 | Gilhuly | |
| 2010/0145222 A1 | 6/2010 | Brunnett et al. | |
| 2010/0198103 A1 | 8/2010 | Meadows et al. | |
| 2010/0210965 A1 | 8/2010 | Gozani et al. | |
| 2010/0249643 A1 | 9/2010 | Gozani et al. | |
| 2010/0286554 A1 | 11/2010 | Davis et al. | |
| 2011/0009768 A1 | 1/2011 | Kosierkiewicz | |
| 2011/0046506 A1 | 2/2011 | Durand et al. | |
| 2011/0071421 A1 | 3/2011 | Gozani et al. | |
| 2011/0264167 A1 | 10/2011 | Poletto | |
| 2012/0046572 A1 | 2/2012 | Odderson | |
| 2012/0065538 A1 | 3/2012 | Friedman | |
| 2012/0083684 A1 | 4/2012 | Kerner et al. | |
| 2012/0116478 A1 | 5/2012 | Buhlmann et al. | |
| 2012/0245482 A1 | 9/2012 | Bolser et al. | |

OTHER PUBLICATIONS

Datex-Ohmeda S/5™ Anesthesia Monitor The clinician's choice, Product Sheet, 2002, 6 pages.
Datex-Ohmeda S/5™ NeuroMuscular Transmission Module, M-NMT, Product Sheet, 2000, 2 pages.
Datex-Ohmeda Cardiocap™/5, Technical Reference Manual, 2$^{nd}$ edition, May 9, 2007, 238 pages.
Engbaek, J., "Monitoring neuromuscular function," Current Opinion in Anaesthesiology, vol. 2, 1989, pp. 479-483.
Erkola, O., et al., "Interaction Between Mivacurium and Succinylcholine," Anesth Analg, vol. 80, 1995, pp. 534-537.
Fiacchino, F., et al., "Submaximal nerve stimulation with the Datex relaxograph NMT monitor in myasthenia gravis," The Italian Journal of Neurological Sciences, vol. 12, No. 6, 1991, pp. 565-568.
GE Healthcare Adequacy of Anesthesia Quick Guide, 2010, 4 pages.
GE Healthcare Avance® Carestation® Product Sheet, 2010, 12 pages.
GE Healthcare Cardiocap™/5, Product Sheet, 2006, 6 pages.
Kahwaji, R., et al., "Dose-Ranging Study in Younger Adult and Elderly Patients of ORG 9487, a New, Rapid-Onset, Short Duration Muscle Relaxant," Anesthesia Analg, vol. 84, 1997, pp. 1011-1018.
Kussman, B., et al., "Administration of magnesium sulfate before rocuronium: effects on speed of onset and duration of neuromuscular block," British Journal of Anaesthesia, vol. 79, 1997, pp. 122-124.
Life-Tech®, Inc., MiniStim® Peripheral Nerve Stimulator, Model MS-IVA, Operator's Manual, 2003, 36 pages.
Mason et al., "Performance assessment of a fuzzy controller for atracurium-induced neuromuscular block," British Journal of Anaesthesia; vol. 76, 1996, pp. 396-400.
Morgan, R.J., et al., "Prediction of infusion rates of vecuronium using the bolus test dose technique," British Journal of Anaesthesia, vol. 74, 1995, pp. 651-654.
Murphy, M.D., G.S., et al., "Part II: Residual Neuromuscular Block," www.anesthesia-analgesia.org, vol. 111, No. 1, Jul. 2010, pp. 129-140.
Polhill, S.L., et al., "Are changes in the evoked electromyogram during anaesthesia without neuromuscular blocking agents caused by failure of supramaximal nerve stimulation," British Journal of Anaesthesia, vol. 81, 1998, pp. 902-904.
Rose, J.B., et al., "The Potency of Succinylcholine in Obese Adolescents," Anesth Analg, vol. 90, 2000, pp. 576-578.
Ross, J.J., et al., "Self-learning fuzzy logic control of neuromuscular block," British Journal of Anaesthesia, vol. 78, 1997, pp. 412-415.
Stewart, P.A., et al., "Critical Respiratory Events and Residual Neuromuscular Blockade in the Postoperative Recovery Unit in 2012," Evolution: Grow Develop Thrive, ANZCA, ASM 2012, Perth Convention and Exhibition Centre, May 12-16, 2012, 8 pages.
Stewart, P.A., "Ipsilateral comparison of acceleromyography and electromyography during recovery from non-depolarizing neuromuscular blockade under general anaesthesia in humans," ANZCA, ASM, Perth, Western Australia, 2012, pp. 493-495.
XAvant Technology, Stimpod NMS450, Features and Benefits, 2011, 2 pages.
Zhou, T.J., et al., "Onset/offset characteristics and intubating conditions of rapacuronium: a comparison with rocuronium," British Journal of Anaesthesia, vol. 85, No. 2, 2000, pp. 246-250.
International Search Report and Written Opinion, dated May 26, 2014, received in connection with International Application No. PCT/US2014/016443.

* cited by examiner

ELECTRODE SYSTEMS FOR USE WITH MEDICAL MONITORING SYSTEMS

CROSS-REFERENCE TO RELATED APPLICATIONS

This application claims the benefit of U.S. Provisional Patent Application No. 61/765,355, filed on Feb. 15, 2013, entitled "ELECTRODE SYSTEMS FOR USE WITH MEDICAL MONITORING SYSTEMS," the disclosure of which is expressly incorporated herein by reference in its entirety.

FIELD OF THE INVENTION

Provided are electrode systems for use with medical monitoring systems. For example, the electrode systems are optionally used with neuromuscular monitoring systems.

BACKGROUND

About 230 million surgeries take place annually worldwide; 40 million US patients undergo in-hospital general anesthesia, which induces loss of consciousness, each year, and 25 million of those also receive muscle relaxants (also called neuromuscular blocking agents, NMBAs), which inhibit neuromuscular transmission. These relaxant agents decrease muscle tension and suppress reflex contractions.

Muscle relaxants (NMBAs) have two forms: depolarizing agents, which are short-acting (5-10 min duration) and are sometimes used at the start of anesthesia to facilitate tracheal intubation, and non-depolarizing agents that have a longer duration of action (20-60 min), and that are used to maintain muscle relaxation during surgery. The effects of non-depolarizing agents start within minutes and continue for up to 20-60 minutes after withdrawal (depending on the type of relaxant used), so they must be administered repeatedly throughout the surgical procedure.

Systems and methods for monitoring neuromuscular function have been proposed. For example, systems and methods for assessing the level of neuromuscular blockade in a subject having been administered NMBAs have been proposed. The systems and methods for monitoring neuromuscular function can include electrode systems for delivering electrical stimulation to a motor nerve of the subject and recording for a corresponding nerve and/or muscle response to the electrical stimulation, for example.

SUMMARY

Electrode systems for use with medical monitoring systems are provided herein. For example, the electrode systems are optionally used with neuromuscular monitoring systems. Methods for manufacturing electrode systems are also provided herein. Additionally, systems and methods for assessing muscle electrical activity of the subject using electrode systems are provided herein.

An example electrode system for use with a monitoring system can include a flexible substrate, a connector interface, one or more stimulating electrodes, one or more recording electrodes and a plurality of conductive traces carried on the flexible substrate. The connector interface can be configured to communicatively connect the electrode system with the monitoring system. In addition, the one or more stimulating electrodes can be configured to deliver an electrical pulse, and the one or more recording electrodes can be configured to receive an electrical signal. The plurality of conductive traces can electrically connect at least one stimulating electrode or at least one recording electrode with the connector interface. Further, each of the one or more stimulating electrodes can have an elongate shape with a length dimension that is substantially greater than a width dimension.

As discussed herein, the length dimension is substantially greater than the width dimension when the length dimension is at least two times greater than the width dimension. Optionally, the length dimension is substantially greater than the width dimension when the length dimension is greater than two times the width dimension. For example, the length dimension is substantially greater than the width dimension when the length dimension is at least three, four, five, six, seven or eight times greater than the width dimension.

Additionally, each of the one or more stimulating electrodes can have a non-rectangular shape. Optionally, each of the one or more stimulating electrodes can have a convex shape. For example, each of the one or more stimulating electrodes can have a triangular, hexagonal, octagonal, etc. shape. Alternatively or additionally, each of the one or more stimulating electrodes can have at least one rounded corner. For example, each of the one or more stimulating electrodes can include first and second sides that define the length dimension. The first and second sides can optionally extend substantially in parallel along the length dimension. In addition, each of the one or more stimulating electrodes can include third and fourth sides that define the width dimension. Optionally, one of the third and forth sides can form the at least one rounded corner, which can connect the first and second sides. Alternatively, the at least one rounded corner can optionally connect one of the first and second side and one of the third and fourth side.

Optionally, each of the one or more stimulating electrodes can have a maximum surface area less than or equal to 1.5 $cm^2$.

Optionally, a surface area of each of the one or more stimulating electrodes can be greater than a surface area of each of the one or more recording electrodes. For example, the surface area of each of the one or more stimulating electrodes can be approximately 1.5 times greater than the surface area of each of the one or more recording electrodes.

The flexible substrate can define proximal and distal ends. Optionally, the connector interface can be disposed at the proximal end of the flexible substrate. Alternatively or additionally, the flexible substrate can include a first portion on which the stimulating electrodes are disposed and a second portion on which the recording electrodes are disposed. Optionally, the first portion can be arranged adjacent to the proximal end of the flexible substrate and the second portion can be arranged adjacent to the distal end of the flexible substrate. Additionally, the second portion can optionally be an elongate portion extending distally from the first portion.

The one or more recording electrodes can optionally include at least two recording electrodes. For example, the recording electrodes can be spaced apart on the second portion of the flexible substrate. Additionally, the recording electrodes can be arranged approximately co-linearly on the second portion of the flexible substrate. In response to bending of the flexible substrate, each of the recording electrodes can be moveable relative to the other recording electrodes or the one or more stimulating electrodes.

In addition, the one or more stimulating electrodes can include at least two stimulating electrodes. For example, the stimulating electrodes can be spaced apart on the first portion of the flexible substrate. Additionally, in response to bending of the flexible substrate, each of the stimulating electrodes can be moveable relative to the other stimulating electrodes.

Optionally, the electrode system can include a dielectric layer carried on the flexible substrate. For example, the dielectric layer can provide electrical insulation between any two of the plurality of conductive traces, the one or more stimulating electrodes and the one or more recording electrodes. Alternatively or additionally, the dielectric layer prevents inadvertent stimulation of the subject's skin through undesired conductive paths.

Optionally, the electrode system can include a foam layer carried on the flexible substrate. Additionally, the foam layer can define a plurality of openings around each of the one or more stimulating electrodes and the one or more recording electrodes. The electrode system can further include a conductive adhesive arranged in at least one of the plurality of openings in the foam layer. The conductive adhesive can be capable of binding to a subject's skin. For example, the conductive adhesive can be a conductive adhesive gel. Alternatively or additionally, the conductive adhesive can be a conductive solid gel or a conductive liquid gel. Alternatively or additionally, the electrode system can include an adhesive layer arranged on the flexible substrate. The adhesive layer can be capable of binding the electrode system to the subject's skin. Further, the electrode system can include a transfer adhesive layer that binds the foam layer and the flexible substrate.

Optionally, the flexible substrate is a polyester film substrate. Additionally, the plurality of conductive traces can optionally be formed from at least one of a conductive silver or silver-carbon ink. Each of the one or more stimulating electrodes and the one or more recording electrodes can optionally include a first layer carried on the flexible substrate and a second layer carried on the first layer. The first layer can be formed from at least one of a conductive silver or silver-carbon ink and the second layer can be formed from a conductive silver-silver chloride ink. In addition, each of the plurality of conductive traces can be connected to the first layer of at least one of the one or more stimulating electrodes and the one or more recording electrodes.

The monitoring system can be configured to deliver an electrical pulse to a subject through the one or more stimulating electrodes. Further, the electrode system can be configured to detect electrical activity of at least one of a muscle response or a nerve response to the delivered electrical pulse using the one or more recording electrodes. Optionally, the monitoring system can be configured to monitor neuromuscular blockade in the subject.

Optionally, the electrode system can include a temperature sensor for measuring a temperature of a subject to which the electrode system is applied. The temperature sensor can be carried on the flexible substrate.

Optionally, the electrode system can include a security IC chip configured to provide authentication between the electrode system and the monitoring system. The security IC chip can be carried on the flexible substrate.

Optionally, the electrode system includes four electrodes. Optionally, the electrode system includes no more than four electrodes. For example, the electrode system may not include a common ground electrode.

In addition, an example method for manufacturing an electrode system can include providing a flexible substrate. The method can further include providing a connector interface, one or more stimulating electrodes, one or more recording electrodes and a plurality of conductive traces on the flexible substrate. The connector interface can be configured to communicatively connect the electrode system with a monitoring system. In addition, the one or more stimulating electrodes can be configured to deliver an electrical pulse, and the one or more recording electrodes can be configured to receive an electrical signal. The plurality of conductive traces can electrically connect at least one stimulating electrode or at least one recording electrode with the connector interface. Further, each of the one or more stimulating electrodes can have an elongate shape with a length dimension that is substantially greater than a width dimension.

As discussed herein, the length dimension is substantially greater than the width dimension when the length dimension is at least two times greater than the width dimension. Optionally, the length dimension is substantially greater than the width dimension when the length dimension is greater than two times the width dimension. For example, the length dimension is substantially greater than the width dimension when the length dimension is at least three, four, five, six, seven or eight times greater than the width dimension.

Additionally, each of the one or more stimulating electrodes can have a non-rectangular shape. Optionally, each of the one or more stimulating electrodes can have a convex shape. For example, each of the one or more stimulating electrodes can have a triangular, hexagonal, octagonal, etc. shape. Alternatively or additionally, each of the one or more stimulating electrodes can have at least one rounded corner. For example, each of the one or more stimulating electrodes can include first and second sides that define the length dimension. The first and second sides can optionally extend substantially in parallel along the length dimension. In addition, each of the one or more stimulating electrodes can include third and fourth sides that define the width dimension. Optionally, one of the third and forth sides can form the at least one rounded corner, which can connect the first and second sides. Alternatively, the at least one rounded corner can optionally connect one of the first and second side and one of the third and fourth side.

Optionally, each of the one or more stimulating electrodes can have a maximum surface area less than or equal to 1.5 $cm^2$.

Optionally, a surface area of each of the one or more stimulating electrodes can be greater than a surface area of each of the one or more recording electrodes. For example, the surface area of each of the one or more stimulating electrodes can be approximately 1.5 times greater than the surface area of each of the one or more recording electrodes.

The flexible substrate can define proximal and distal ends. Optionally, the connector interface can be disposed at the proximal end of the flexible substrate. Alternatively or additionally, the flexible substrate can include a first portion on which the stimulating electrodes are disposed and a second portion on which the recording electrodes are disposed. Optionally, the first portion can be arranged adjacent to the proximal end of the flexible substrate and the second portion can be arranged adjacent to the distal end of the flexible substrate. Additionally, the second portion can optionally be an elongate portion extending distally from the first portion.

The one or more recording electrodes can optionally include at least two recording electrodes. For example, the recording electrodes can be spaced apart on the second portion of the flexible substrate. Additionally, the recording electrodes can be arranged approximately co-linearly on the second portion of the flexible substrate. In response to bending of the flexible substrate, each of the recording electrodes can be moveable relative to the other recording electrodes or the one or more stimulating electrodes.

In addition, the one or more stimulating electrodes can include at least two stimulating electrodes. For example, the stimulating electrodes can be spaced apart on the first portion of the flexible substrate. Additionally, in response to bending of the flexible substrate, each of the stimulating electrodes can be moveable relative to the other stimulating electrodes.

Optionally, the method can further include providing a dielectric layer on the flexible substrate. For example, the dielectric layer can provide electrical insulation between any two of the plurality of conductive traces, the one or more stimulating electrodes and the one or more recording electrodes. Alternatively or additionally, the dielectric layer prevents inadvertent stimulation of the subject's skin through undesired conductive paths.

Optionally, the method can further include providing a foam layer on the flexible substrate. Additionally, the foam layer can define a plurality of openings around each of the one or more stimulating electrodes and the one or more recording electrodes. The method can further include providing a conductive adhesive arranged in at least one of the plurality of openings in the foam layer. The conductive adhesive can be capable of binding to a subject's skin. For example, the conductive adhesive can be a conductive adhesive gel. Alternatively or additionally, the conductive adhesive can be a conductive solid gel or a conductive liquid gel. Alternatively or additionally, the method can include providing an adhesive layer on the flexible substrate. The adhesive layer can be capable of binding the electrode system to the subject's skin. Further, the method can include providing a transfer adhesive layer that binds the foam layer and the flexible substrate.

Optionally, the flexible substrate is a polyester film substrate. Additionally, the plurality of conductive traces can optionally be formed from at least one of a conductive silver or silver-carbon ink. Optionally, the method can include printing at least one of a conductive silver or silver-carbon ink on the flexible substrate. Each of the one or more stimulating electrodes and the one or more recording electrodes can optionally include a first layer carried on the flexible substrate and a second layer carried on the first layer. The first layer can be formed from at least one of a conductive silver or silver-carbon ink and the second layer can be formed from a conductive silver-silver chloride ink. For example, the method can optionally include printing the first layer formed from the at least one of a conductive silver or silver-carbon ink on the flexible substrate and printing the second layer formed from the conductive silver-silver chloride ink on the first layer. In addition, each of the plurality of conductive traces can be connected to the first layer of at least one of the one or more stimulating electrodes and the one or more recording electrodes.

Optionally, the method can further include providing a temperature sensor for measuring a temperature of a subject to which the electrode system is applied on the flexible substrate.

Optionally, the method can further include providing a security IC chip configured to provide authentication between the electrode system and the monitoring system on the flexible substrate.

Optionally, the electrode system includes four electrodes. Optionally, the electrode system includes no more than four electrodes. For example, the electrode system may not include a common ground electrode.

In addition, an example system for assessing muscle electrical activity in a subject includes a motor nerve stimulator configured generate an electrical pulse to stimulate a targeted motor nerve of the subject and a recording apparatus for recording electrical activity of a muscle innervated by the motor nerve. The system can also include an electrode system including a flexible substrate, a connector interface, one or more stimulating electrodes, one or more recording electrodes and a plurality of conductive traces carried on the flexible substrate. The connector interface can be configured to communicatively connect the electrode system with the monitoring system. In addition, the one or more stimulating electrodes can be configured to deliver an electrical pulse, and the one or more recording electrodes can be configured to receive an electrical signal. The plurality of conductive traces can electrically connect at least one stimulating electrode or at least one recording electrode with the connector interface. Further, each of the one or more stimulating electrodes can have an elongate shape with a length dimension that is substantially greater than a width dimension. Alternatively or additionally, the electrode system can be any of the electrode systems provided herein.

An example method for assessing neuromuscular blockade in a subject having been administered a muscle relaxant agent can include stimulating a motor nerve to cause an evoked muscle response by applying a stimulus using one or more stimulating electrodes and recording for electrical activity of a muscle innervated by the motor nerve using one or more recording electrodes. The method can further include determining a level of neuromuscular blockade in the subject using the recorded electrical activity. Additionally, each of the one or more stimulating electrodes can have an elongate shape with a length dimension that is substantially greater than a width dimension. Alternatively or additionally, the one or more stimulating electrodes can be any of the stimulating electrodes provided herein.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. While implementations will be described for electrode systems for use with neuromuscular monitoring systems, it will become evident to those skilled in the art that the implementations are not limited thereto, but are applicable for electrode systems for use with other types of systems.

As discussed above, electrode systems for use with medical monitoring systems are provided herein. For example, the electrode systems are optionally used with neuromuscular monitoring systems. Methods for manufacturing and using the electrode systems are also provided herein. An example electrode system can include one or more stimulating electrodes and one or more recording electrodes carried on a flexible substrate. Additionally, the electrode system can include a connector interface carried on the flexible substrate. The connector interface can be configured to communicatively connect the electrode system with the monitoring system. A plurality of conductive traces carried on the flexible substrate can electrically connect at least one stimulating electrode or at least one recording electrode with the connector interface.

The electrode system is optionally used when performing neuromuscular monitoring on different subjects. Additionally, the electrode system is optionally used when performing neuromuscular monitoring at different anatomical locations. For example, neuromuscular monitoring can be performed at different nerves and/or muscles of one or more subject. The electrode system can therefore be designed to reach the desired anatomical locations of the subjects based on the expected size range of the subjects and/or the desired anatomical locations. The electrode system facilitates placement of the one or more stimulating and the one or more recording electrodes on the subjects. Optionally, the electrode system can guide a medical professional and/or other system operator in correctly placing the one or more stimulating and the one or more recording electrodes on the subject at the desired anatomical locations. Further, the electrode system facilitates connecting the electrode system and the monitoring system.

Figure 1:
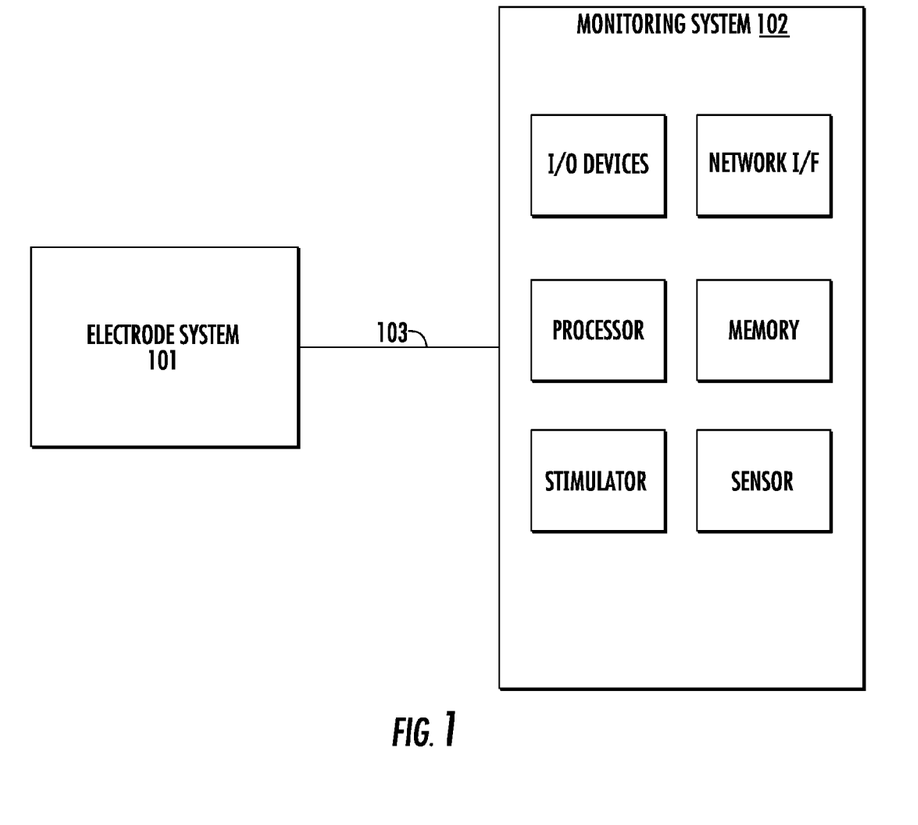
FIG. 1 is a block diagram illustrating an electrode system communicatively connected to a monitoring system according to an example implementation.

Referring now to FIG. 1, a block diagram illustrating an example electrode system 101 communicatively connected to a neuromuscular monitoring system 102 is shown. The electrode system 101 is communicatively connected to the monitoring system 102 through a communication link 103. The communication link 103 can be implemented using any medium that facilitates the exchange of signals between the electrode system 101 and the monitoring system 102. The electrode system 101 is the interface for delivering/detecting electrical signals to/from a subject. The subject or patient discussed herein can be human and non-human animals of any age. The electrode system 101 is discussed in detail below with regard to FIGS. 2A-4B.

The monitoring system 102 can be a neuromuscular monitoring system, for example. It should also be understood that this disclosure contemplates that the monitoring system 102 can be any type of monitoring system including, but not limited to, a neuromuscular function testing system. The monitoring system 102 can include a processor and memory. The processor can be configured to execute program code encoded in tangible, computer-readable media. The processor can be configured to execute program code stored in the memory. Computer-readable media refers to any media capable of providing data that causes the monitoring system 102 to operate in a particular fashion. For example, the computer-readable media can store program code that causes the monitoring system 102 to assess the level of neuromuscular blockade in a subject. Computer-readable media includes volatile and non-volatile media implemented in any method or technology for storage of information such as computer readable instructions, data structures, program modules or other data.

Additionally, the monitoring system 102 can include a stimulator configured to generate an electrical pulse. The stimulator can optionally be configured to generate a train of electrical pulses (e.g., train-of-four, tetanic, etc.). Each of the electrical pulses can be delivered to a motor nerve of the subject such as the median or ulnar nerve at the wrist, the tibial nerve at the ankle, the facial nerve beneath the ear, etc. Each of the electrical pulses can be of sufficient strength to elicit a nerve response. The stimulator can include circuitry for filtering, amplifying, and/or otherwise conditioning each of the electrical pulses. Each of the electrical pulses can then be delivered to the subject using the electrode system 101. In addition, the monitoring system 102 can include a sensor configured to detect an electrical signal from the subject. For example, the sensor can be configured to detect a nerve response and/or a muscle response to each of the electrical pulses delivered to the motor nerve. Similar to the stimulator, the sensor can include circuitry for filtering, amplifying, and/or otherwise conditioning the detected electrical signals. The electrode system 101 can be the interface for delivering each of the electrical pulses generated and optionally conditioned by the stimulator to the subject and for receiving the raw detected electrical signals from the subject.

The monitoring system 102 can also optionally include input/output devices and network interfaces. Input devices include a keyboard, touch screen, mouse, button, dial, switch, etc. Output devices include a display screen, speaker, printer, etc. Network interfaces are devices that facilitate communication between the monitoring system 102 and other devices. Input/output devices and network interfaces are well known in the art and need not be discussed at length here.

Figure 2A:
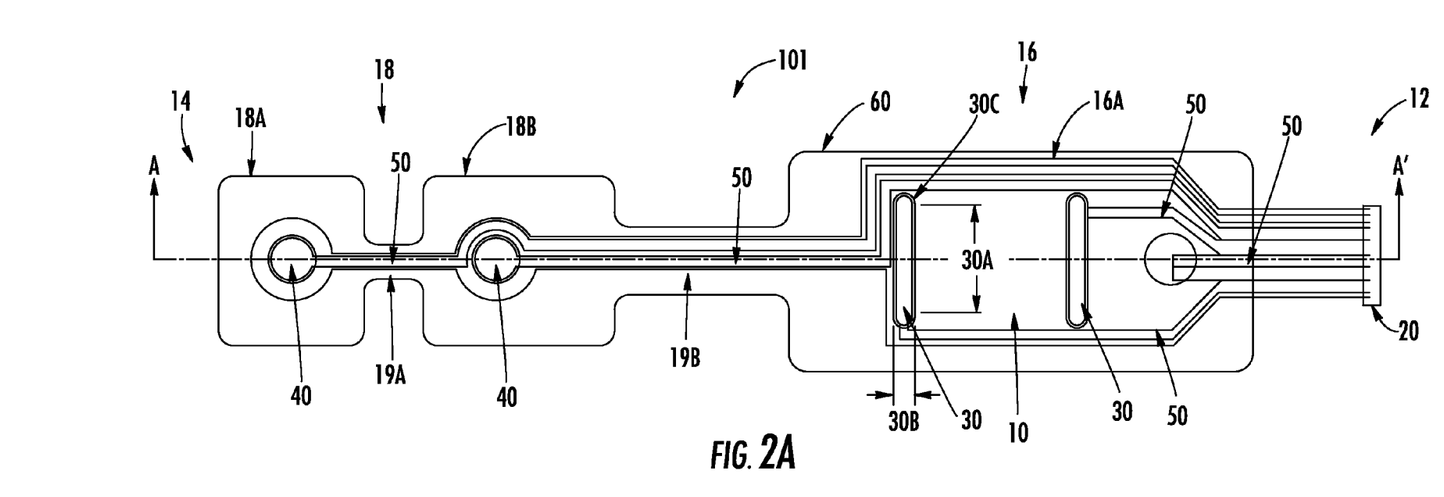
FIGS. 2A-2B are plan and sectional views illustrating an electrode system according to an example implementation discussed herein.
Figure 2B:
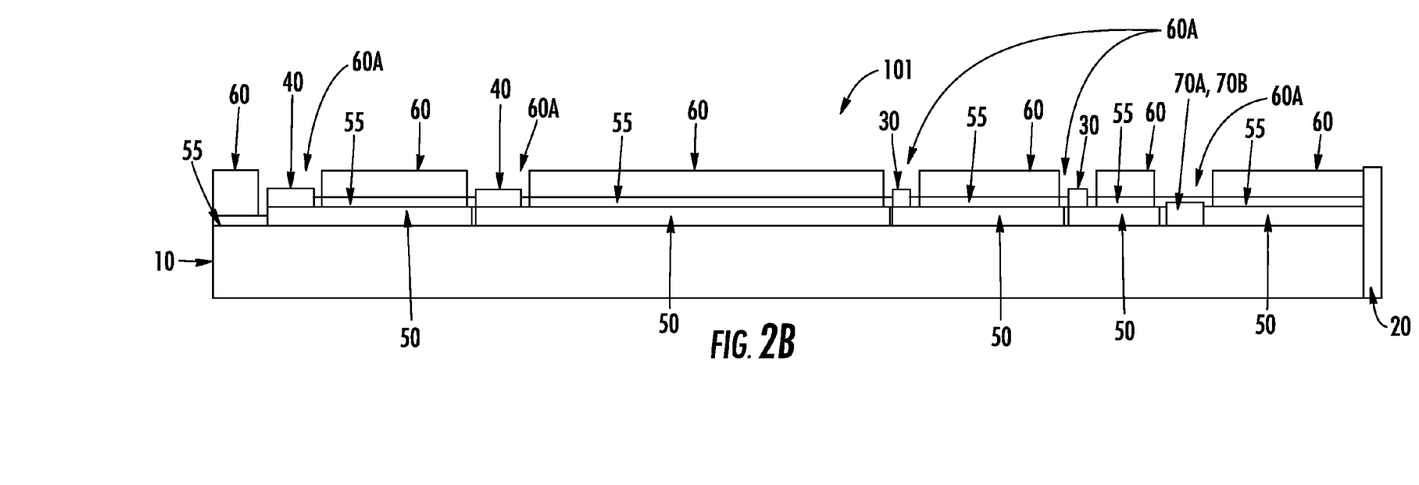

Referring now to FIGS. 2A-2B, plan and sectional views illustrating an electrode system 101 are shown. FIG. 2B is a sectional view taken along the dashed line A-A' of FIG. 2A. The electrode system 101 can include a flexible substrate 10. The flexible substrate 10 can optionally be a polyester film substrate (e.g., MYLAR). Alternatively, the flexible substrate 10 can be any material providing the desired stiffness and/or flexibility. For example, the flexible substrate 10 can be formed from a material providing sufficient stiffness to allow the medical professional to manipulate the electrode system 101 and place the electrodes on the subject. Additionally, the flexible substrate 10 can be formed from a material providing sufficient flexibility to allow the medical professional to move the electrodes relative to each other. The flexible substrate 10 can define a proximal end 12 and a distal end 14. Additionally, the flexible substrate 10 can include a first portion 16 on which one or more stimulating electrodes 30 are carried and a second portion 18 on which one or more recording electrodes 40 are carried. For example, the stimulating electrodes 30 can be carried on an island 16A, and the recording electrodes 40 can be carried on islands 18A, 18B. Each of the stimulating electrodes 30 and the recording electrodes 40 can optionally be carried on separate islands. Although FIGS. 2A-4B show electrode systems having two stimulating electrodes and two recording electrodes, this disclosure contemplates electrode systems having more or fewer stimulating and/or recording electrodes. Each of the islands 16A, 18A, 18B can optionally be connected by a bridge portion 19A, 19B. The first portion 16 can optionally be arranged adjacent to the proximal end 12 of the flexible substrate 10, and the second portion 18 can optionally be arranged adjacent to the distal end 14 of the flexible substrate 10.

For example, as shown in FIGS. 2A-2B, two stimulating electrodes 30 can be arranged in a spaced apart pattern on the island 16A. Because of the flexibility of the flexible substrate 10, each of the stimulating electrodes 30 is moveable relative to the other stimulating electrodes 30. For example, the medical professional can place the stimulating electrodes 30 in the desired anatomical location such as in proximity to a motor nerve of the subject. Alternatively or additionally, the second portion 18 can optionally be an elongated portion extending distally from the first portion 16. As shown in FIGS. 2A-2B, the second portion 18 can optionally include two separate islands 18A, 18B on which each recording electrode 40 is carried. The islands 18A, 18B and corresponding recording electrodes 40 can be arranged in a spaced apart pattern. Optionally, the islands 18A, 18B and corresponding recording electrodes 40 can be arranged approximately co-linearly. The second portion 18 can optionally be more flexible than the first portion 16 due to its more elongate geometry as compared to the first portion 16. Additionally, because of the flexibility of the flexible substrate 10, each of the recording electrodes 40 is moveable relative to the other recording electrodes 40 and/or the one or more stimulating electrodes 30. This facilitates the medical professional in properly positioning the one or more recording electrodes 40 in the desired anatomical location. For example, the medical professional can place one of the one or more recording electrodes 40 in proximity to a muscle innervated by the motor nerve and one of the one or more recording electrodes 40 at another anatomical location (e.g., spaced from the muscle innervated by the motor nerve) in order to record the muscle electrical activity in response to motor nerve stimulation as a differential signal.

In addition, the electrode system 101 can include a connector interface 20 carried on the flexible substrate 10. For example, the connector interface 20 can optionally be disposed at the proximal end 12 of the flexible substrate 10. The connector interface 20 can facilitate connecting the electrode system 101 and the monitoring system (e.g., the monitoring system 102 shown in FIG. 1). The connector interface 20 can communicatively connect the electrode system 101 and the monitoring system such that electrical pulses are passed from the monitoring system to the electrode system 101 for delivery to the subject via the one or more stimulating electrodes 30. Alternatively or additionally, electrical signals (e.g., muscle electrical activity) from the subject are detected with the one or more recording electrodes 40 of the electrode system 101 and delivered to the monitoring system for further processing. The monitoring system can process the electrical signals to assess the level of neuromuscular blockade in the subject, for example. The electrode system 101 can include a plurality of conductive traces 50 carried on the flexible substrate 10. The conductive traces 50 can electrically connect at least one stimulating electrode 30 or at least one recording electrode 40 with the connector interface 20. As shown in FIGS. 2A-2B, each of the one or more stimulating electrodes 30 and each of the one or more recording electrodes 40 is electrically connected to the connector interface 20 through a conductive trace 50.

The conductive traces 50 can be a conductive pattern deposited on the flexible substrate 10 by any means known in the art including, but not limited to, screening, printing, chemical plating, etc. The conductive traces 50 can be formed of a conductive ink such as silver ink or a mixture of silver and carbon ink, for example. The silver-carbon ink creates conductive traces with lower resistance as compared to carbon ink traces at a reduced cost as compared to silver ink traces. The stimulating and/or recording electrodes 30, 40 can also be a conductive pattern deposited on the flexible substrate 10 by any means known in the art. Similar to the conductive traces 50, at least a portion of the stimulating and recording electrodes 30, 40 can be formed of a conductive ink such as silver ink or a mixture of silver and carbon ink, for example. Optionally, at least a portion of the stimulating and/or recording electrodes 30, 40 can also be formed from a mixture of silver and silver chloride ink. By adding silver chloride to the silver ink, the stimulating and/or recording electrodes 30, 40 are more reversible. For example, silver chloride can be provided in an approximately 20% concentration to the silver. Optionally, the silver-silver chloride ink can be used only for a portion of each of the stimulating and/or recording electrodes 30, 40. The silver-silver chloride ink is more corrosive and can potentially corrode other portions of the electrode system 101 such as the connector interface 20, for example. The stimulating and/or recording electrodes 30, 40 can include a first layer of silver ink and/or silver-carbon ink carried on the flexible substrate 10 and a second layer of silver-silver chloride ink carried on the first layer. Optionally, the conductive traces 50 and at least a portion of the stimulating and recording electrodes 30, 40 can be deposited on the flexible substrate 10 as a conductive ink (e.g., silver and/or silver-carbon ink) in a first step, and at least a portion of the stimulating and/or recording electrodes 30, 40 can be deposited as a conductive ink (e.g., silver-silver chloride ink) in a second step.

Optionally, the electrode system 101 can include a temperature sensor 70A for measuring a temperature of the subject to which the electrode system 101 is applied. It should be understood that the temperature of the subject's skin effects neuromuscular testing and monitoring. For example, colder nerves have lower conduction velocities as compared to warmer nerves. The temperature of the subject's skin provides an indication of the temperature of the subject's nerves. The temperature measured by the temperature sensor 70A can be used by the monitoring system 102, for example, to notify the medical professional when the subject's skin temperature is too low to obtain accurate results, to provide temperature compensation, etc. The temperature sensor 70A can optionally be carried on the flexible substrate 10. Additionally, one or more of the conductive traces 50 can electrically connect the temperature sensor 70A and the connector interface 20.

Alternatively or additionally, the electrode system 101 can include a security IC chip 70B configured to provide authentication between the electrode system 101 and the monitoring system (e.g., the monitoring system 102 shown in FIG. 1). For example, the monitoring system can be configured to read or otherwise obtain a unique identifier from the security IC chip 70B. Optionally, the unique identifier can be encoded, and the monitoring system can decode the unique identifier. The security IC chip 70B can be carried on the flexible substrate 10. Additionally, one or more of the conductive traces 50 can electrically connect the security IC chip 70B and the connector interface 20.

The electrode system 101 can also include a dielectric layer 55 carried on the flexible substrate 10. The dielectric layer 55 provides electrical insulation. For example, the dielectric layer 55 prevents shorting between any two of the plurality of conductive traces 50, the one or more stimulating electrodes 30 and the one or more recording electrodes 40. Alternatively or additionally, the dielectric layer 55 prevents inadvertent stimulation of the subject's skin through undesired conductive paths. The dielectric layer 55 can be provided on the flexible substrate 10 by any means known in the art. For example, the dielectric layer 55 can be provided over one or more portions of the flexible substrate 10. Optionally, the dielectric layer 55 can be provided over the flexible substrate 10 after the conductive traces 50, the one or more stimulating electrodes 30 and/or the one or more recording electrodes 40 are provided on the flexible substrate 10. The dielectric layer 55 can be provided over at least portions of the conductive traces 50, the one or more stimulating electrodes 30 and/or the one or more recording electrodes 40. Optionally, the dielectric layer 55 can be provided such that areas adjacent to the one or more stimulating electrodes 30, the one or more recording electrodes 40 or the temperature sensor 70A and/or security IC chip 70B remain uncovered by the dielectric layer 55.

Optionally, the electrode system 101 can include a foam layer 60 carried on the flexible substrate 10. The foam layer 60 can optionally be provided on one or both sides of the flexible substrate 10. Further, the electrode system 101 can include a transfer adhesive layer that binds the foam layer 60 and the flexible substrate 10. Additionally, the foam layer 60 can define a plurality of openings 60A around each of the one or more stimulating electrodes 30, the one or more recording electrodes 40, the temperature sensor 70A and/or the security IC chip 70B. For example, the foam layer 60 can be pre-cut with a plurality of openings 60A before being secured to the flexible substrate 10. A conductive adhesive can optionally be provided in at least one of the plurality of openings 60A such as the openings 60A around one or more of the stimulating and/or recording electrodes 30, 40. For example, the plurality of openings 60A can act as wells for holding the conductive adhesive. The conductive adhesive can be capable of binding to the subject's skin. The conductive adhesive can also be capable of electrically coupling the one or more stimulating electrodes 30 and/or recording electrodes 40 to the subject's skin. For example, the conductive adhesive can be a conductive adhesive gel. Alternatively or additionally, the conductive adhesive can be a conductive solid gel or a conductive liquid gel. Alternatively or additionally, the electrode system 101 can include an adhesive layer carried on the flexible substrate. The adhesive layer can be capable of binding the electrode system 101 to the subject's skin.

Each of the one or more stimulating electrodes 30 can have an elongate shape with a length dimension 30A that is substantially greater than a width dimension 30B. It is possible to minimize sensitivity to placement of the stimulating electrodes 30 when the stimulating electrodes have an elongate shape. For example, when the stimulating electrodes 30 have an elongate shape, the stimulating electrodes 30 can transect a targeted nerve more easily. In other words, the medical provider can correctly position the stimulating electrodes at the desired anatomical location such as in proximity to a motor nerve of the subject, for example, more easily when the stimulating electrodes 30 have an elongate shape. For example, the length dimension 30A is substantially greater than the width dimension 30B when the length dimension 30A is at least two times greater than the width dimension 30B. Optionally, the length dimension 30A is substantially greater than the width dimension 30B when the length dimension 30A is greater than two times the width dimension 30B. For example, the length dimension 30A is substantially greater than the width dimension 30B when the length dimension 30A is at least three, four, five, six, seven or eight times greater than the width dimension 30B.

Additionally, each of the one or more stimulating electrodes 30 can optionally have a non-rectangular shape. For example, as shown in FIGS. 2A-2B, each of the one or more stimulating electrodes 30 can optionally have at least one rounded corner 30C. It is possible to minimize current density, and in particular local current density peaks, by providing stimulating electrodes 30 with at least one rounded corner 30C. Each of the one or more stimulating electrodes 30 can optionally include first and second sides that define the length dimension 30A. The first and second sides can optionally extend substantially in parallel along the length dimension 30A. In addition, each of the one or more stimulating electrodes 30 can include third and fourth sides that define the width dimension 30B. Optionally, one of the third and forth sides can be the at least one rounded corner 30C, which can connect the first and second sides. Alternatively or additionally, each of the third and forth sides can be the at least one rounded corner 30C, which connect the first and second sides at opposite ends of each of the stimulating electrodes 30. Alternatively, the at least one rounded corner can optionally connect one of the first and second side and one of the third and fourth side. For example, the third and fourth sides can optionally can optionally extend substantially in parallel along the width dimension 30B, and the at least one rounded corner can optionally connect one of the first and second side and one of the third and fourth side. Optionally, each of four corners of each of the stimulating electrodes 30 can be a rounded corner. Alternatively or additionally, each of the one or more stimulating electrodes 30 can have a convex shape. Optionally, each of the one or more stimulating electrodes 30 can have a strictly convex shape, e.g., each internal angle is less than 180 degrees. For example, each of the one or more stimulating electrodes 30 can have a triangular, hexagonal, octagonal, etc. shape. Optionally, the one or more stimulating electrodes 30 having a convex shape can have one or more rounded corners.

Optionally, each of the one or more stimulating electrodes 30 can have a maximum surface area less than or equal to 1.5 $cm^2$. By providing stimulating electrodes 30 with a maximum surface area less than or equal to 1.5 $cm^2$, it is possible to deliver an electrical pulse with sufficient current density to the subject's skin to stimulate a nerve of the subject. Alternatively or additionally, a surface area of each of the one or more stimulating electrodes 30 can be greater than a surface area of each of the one or more recording electrodes 40. For example, the surface area of each of the one or more stimulating electrodes 30 can be approximately 1.5 times greater than the surface area of each of the one or more recording electrodes 40.

The electrode system 101 can optionally be capable of detecting the corresponding nerve and/or muscle response to a stimulated nerve as a floating differential signal with the one or more recording electrodes 40. The floating differential signal can be a non-ground referenced differential signal, for example. Optionally, the electrode system 101 does not include a common ground electrode. Optionally, the electrode system 101 is a four-electrode system. Optionally, the electrode system 101 includes no more than four electrodes. For example, the electrode system 101 can only include two recording electrodes 40 for detecting a floating differential signal and two stimulating electrodes 30 for delivering an electrical pulse.

Figure 3A:
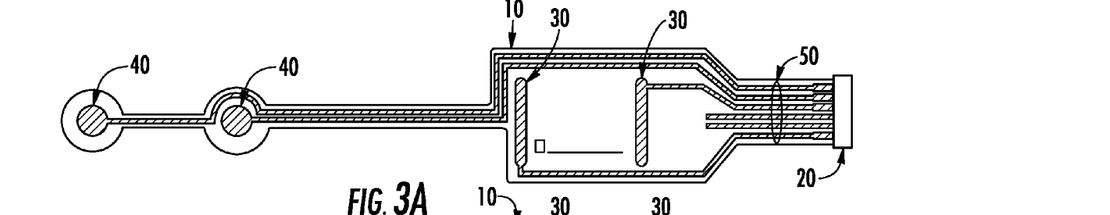
FIGS. 3A-3F are plan views illustrating the electrode system shown in FIGS. 2A-2B.
Figure 3B:
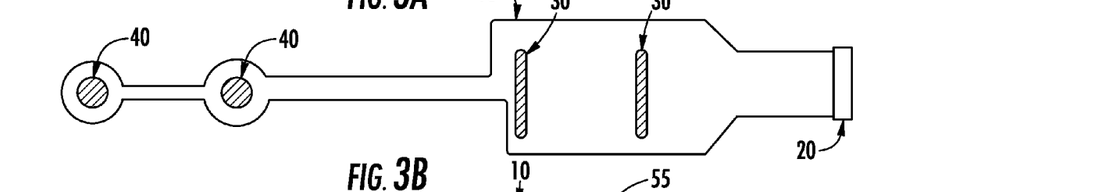

Referring now to FIGS. 3A-3F, an example method for manufacturing an electrode system according to any of the implementations discussed herein is also provided. The method can include providing a flexible substrate 10. The conductive traces 50 can be provided as a conductive pattern deposited on the flexible substrate 10 by any means known in the art including, but not limited to, screening, printing, chemical plating, etc. Additionally, at least a portion of the stimulating and/or recording electrodes 30, 40 can be provided as a conductive pattern deposited on the flexible substrate 10 by any means known in the art. The conductive traces 50 and at least a portion of the stimulating and/or recording electrodes 30, 40 are shaded in FIG. 3A. The conductive traces 50 can electrically connect at least one of the stimulating electrodes 30, the recording electrodes 40, a temperature sensor or a security IC chip with the connector interface 20. As discussed above, the conductive traces 50, stimulating electrodes and/or recording electrodes 30, 40 (including any portion thereof) can be formed of a conductive ink such as silver ink or a mixture of silver and carbon ink, for example. Optionally, at least a portion of the stimulating and/or recording electrodes 30, 40 can also be formed from a mixture of silver and silver chloride ink. As shown in FIG. 3B, the silver-silver chloride ink (shaded in FIG. 3B) can be provided only over the stimulating and/or recording electrodes 30, 40. For example, as discussed above, the stimulating and/or recording electrodes 30, 40 can include a first layer of silver ink and/or silver-carbon ink carried on the flexible substrate 10 (e.g., as shown by the shading in FIG. 3A) and a second layer of silver-silver chloride ink carried on the first layer (e.g., as shown by shading in FIG. 3B). Optionally, the conductive traces 50 and at least a portion of the stimulating and/or recording electrodes 30, 40 can be deposited on the flexible substrate 10 as a conductive ink (e.g., silver and/or silver-carbon ink) in a first step, and at least a portion of the stimulating and/or recording electrodes can be deposited as a conductive ink (e.g., silver-silver chloride ink) in a second step. Optionally, a temperature sensor and/or a security IC chip can be provided on the flexible substrate 10 as discussed above.

Figures 3C, 3D:
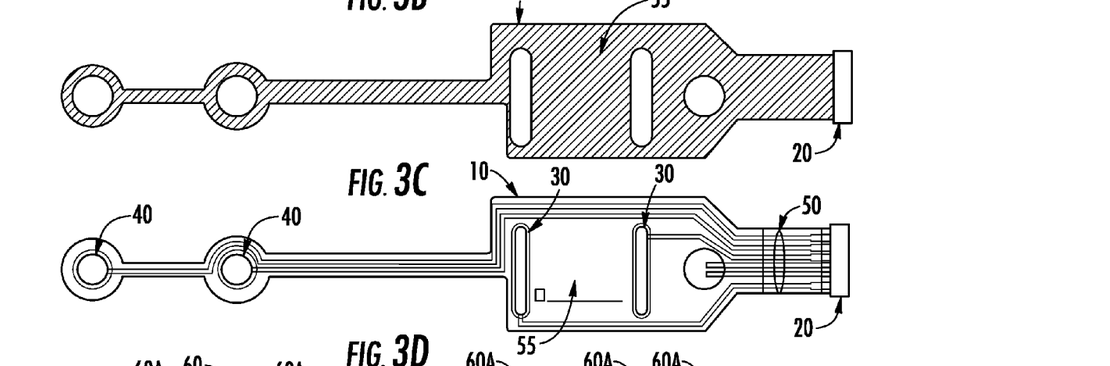

A dielectric layer 55 can optionally be provided on the flexible substrate 10 by any means known in the art. The dielectric layer 55 is discussed in detail above. For example, the dielectric layer 55 can be provided over one or more portions of the flexible substrate 10. The dielectric portion is shaded in FIG. 3C. Optionally, the dielectric layer 55 can be provided over the flexible substrate 10 after the conductive traces 50, the one or more stimulating electrodes 30 and the one or more recording electrodes 40 are provided on the flexible substrate 10. The dielectric layer 55 can be provided over at least portions of the conductive traces 50, the one or more stimulating electrodes 30 or the one or more recording electrodes 40. Optionally, the dielectric layer 55 can be provided such that areas adjacent to the one or more stimulating electrodes 30, the one or more recording electrodes 40 or the temperature sensor and/or security IC chip remain uncovered by the dielectric layer 55. This is shown in FIG. 3D.

Figure 3E:
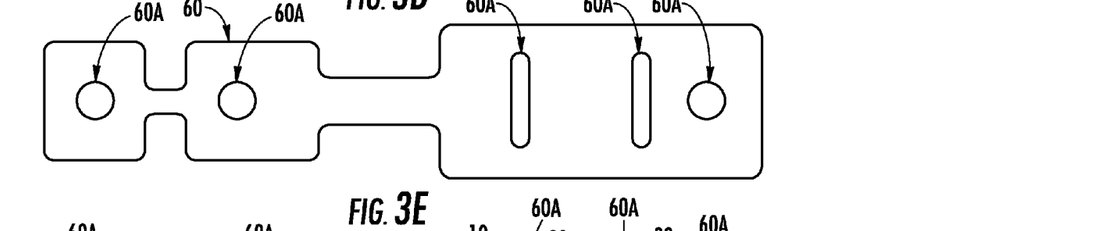
Figure 3F:
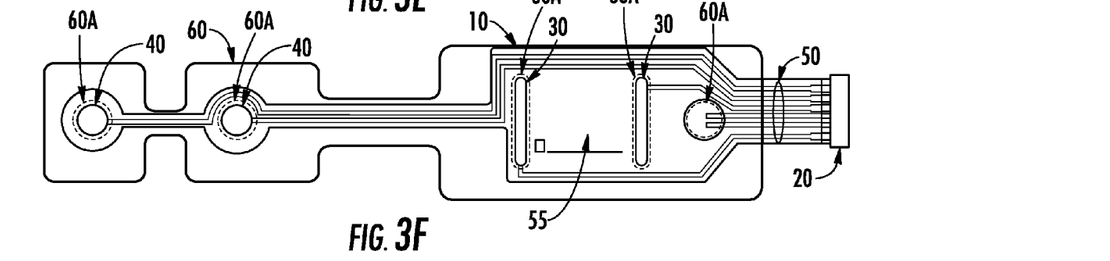

Alternatively or additionally, a foam layer 60 can be provided on the flexible substrate 10. The foam layer 60 is discussed in detail above. The foam layer 60 can optionally be provided on one or both sides of the flexible substrate 10. As shown in FIG. 3E, the foam layer 60 can be pre-cut with a plurality of openings 60A before being secured to the flexible substrate 10. Thereafter, the foam layer 60 can be secured to the flexible substrate 10 with a transfer adhesive, for example, as shown in FIG. 3F. As discussed above, the foam layer 60 can define a plurality of openings 60A around each of the one or more stimulating electrodes 30, the one or more recording electrodes 40, the temperature sensor and/or the security IC chip. The plurality of openings 60A can act as wells for holding a conductive adhesive that is capable of binding to the subject's skin and electrically coupling the one or more stimulating electrodes and/or recording electrodes 30, 40 to the subject's skin.

Figure 4A:
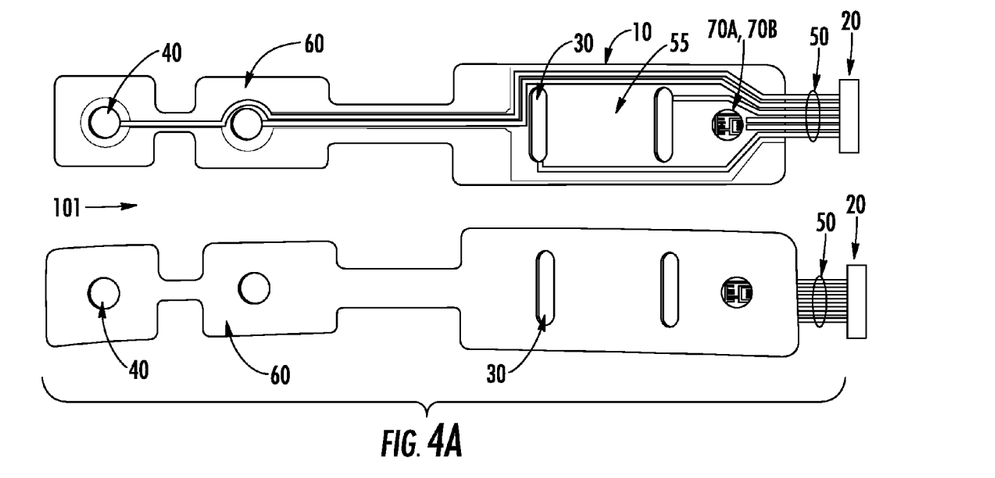
FIGS. 4A-4B are front and back views illustrating the electrode system shown in FIGS. 2A-2B.
Figure 4B:
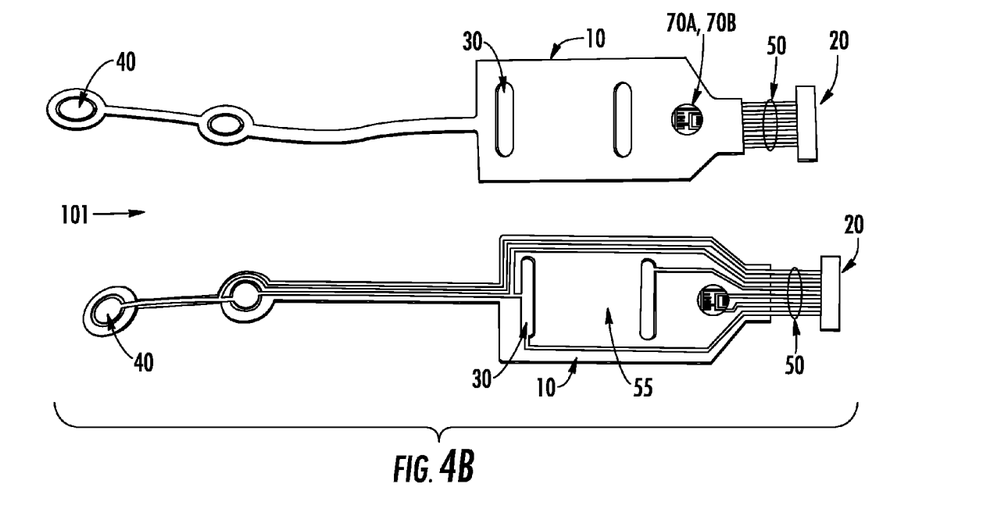

FIGS. 4A-4B are front and back views illustrating the electrode system according to implementations discussed herein. FIG. 4A illustrates front and back views of the electrode system including the foam layer. FIG. 4B illustrates front and back views of the electrode system without a foam layer. As discussed above, the electrode system 101 can optionally include a flexible substrate 10, one or more stimulating electrodes 30, one or more recording electrodes 40, a plurality of conductive traces 50, a dielectric layer 55, a foam layer 60, a connector interface 20 and a temperature sensor or security IC chip 70A, 70B.

Also provided herein are methods for performing neuromuscular monitoring using the electrode system according to any of the implementations discussed herein. For example, neuromuscular monitoring can include assessing muscle electrical activity in a subject. This assessment can include assessing the level of neuromuscular blockade in a subject having been administered a muscle relaxant agent. For example, a motor nerve can be stimulated to cause an evoked muscle response by applying a stimulus using one or more stimulating electrodes 30, and electrical activity of a muscle innervated by the motor nerve can be recorded using one or more recording electrodes 40. The level of neuromuscular blockade in the subject can be determined using the recorded electrical activity.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An electrode system comprising:
a flexible substrate having a length axis and a width axis, wherein said length axis is substantially greater than said width axis, said flexible substrate comprising no more than three islands and bridges between the islands;
a connector interface carried on the flexible substrate and configured to communicatively connect the electrode system with a monitoring system;
one or more stimulating electrodes carried on a first island of the flexible substrate, said one or more stimulating electrodes configured to deliver an electrical pulse;
a first bridge that connects the first island to a second island and a second bridge that connects the second island to a third island;
no more than one recording electrodes carried on the second island of the flexible substrate and configured to detect an electrical signal;
one recording electrode carried on the third island of the flexible substrate and configured to detect an electrical signal; and
a plurality of conductive traces carried on the flexible substrate, wherein a first one of the plurality of conductive traces routes across the first island, the first bridge, the second island, and the second bridge to electrically connect the one recording electrode carried on the third island with the connector interface, and wherein a second one of the plurality of conductive traces routes across the first island and the first bridge to electrically connect the no more than one recording electrode carried on the second island with the connector interface, and wherein a third one or more of the plurality of conductive traces electrically connect the one or more stimulating electrodes carried on the first island with the connector interface, wherein each of the one or more stimulating electrodes has a rectangular-elongate shape with a length dimension that is at least two times greater than a width dimension and said length dimension is substantially perpendicular to the length axis of the flexible substrate.

2. The electrode system of claim 1, wherein the length dimension is at least five times greater than the width dimension.

3. The electrode system of claim 1, wherein each of the one or more stimulating electrodes has at least one rounded corner.

4. The electrode system of claim 3, wherein each of the one or more stimulating electrodes comprises first and second sides that define the length dimension.

5. The electrode system of claim 4, wherein the first and second sides extend substantially in parallel along the length dimension.

6. The electrode system of claim 4, wherein each of the one or more stimulating electrodes comprises third and fourth sides that define the width dimension.

7. The electrode system of claim 6, wherein one of the third and fourth sides forms the at least one rounded corner, the at least one rounded corner connecting the first and second sides.

8. The electrode system of claim 6, wherein the at least one rounded corner connects one of the first and second side and one of the third and fourth side.

9. The electrode system of claim 1, wherein each of the one or more stimulating electrodes has a maximum surface area less than or equal to 1.5 cm$^2$.

10. The electrode system of claim 1, wherein the flexible substrate defines proximal and distal ends, the connector interface being disposed at the proximal end of the flexible substrate.

11. The electrode system of claim 1, wherein the one or more stimulating electrodes comprise at least two stimulating electrodes, the stimulating electrodes being spaced apart on the first island of the flexible substrate.

12. The electrode system of claim 1, further comprising a dielectric layer carried on the flexible substrate, the dielectric layer providing electrical insulation between any two of the plurality of conductive traces, the one or more stimulating electrodes and the recording electrodes.

13. The electrode system of claim 1, further comprising a foam layer carried on the flexible substrate, wherein the foam layer defines a plurality of openings around each of the one or more stimulating electrodes and the recording electrodes.

14. The electrode system of claim 13, further comprising a conductive adhesive arranged in at least one of the plurality of openings in the foam layer, the conductive adhesive capable of binding to a subject's skin.

15. The electrode system of claim 13, further comprising a transfer adhesive layer that binds the foam layer and the flexible substrate.

16. The electrode system of claim 1, wherein the plurality of conductive traces are formed from at least one of a conductive silver or silver-carbon ink.

17. The electrode system of claim 1, wherein each of the one or more stimulating electrodes and the recording electrodes comprises a first layer carried on the flexible substrate and a second layer carried on the first layer, the first layer being formed from at least one of a conductive silver or silver-carbon ink and the second layer being formed from a conductive silver-silver chloride ink.

18. The electrode system of claim 17, wherein each of the plurality of conductive traces is connected to the first layer of at least one of the one or more stimulating electrodes and the recording electrodes.

19. The electrode system of claim 1, wherein the one or more stimulating electrodes are configured to deliver the electrical pulse to a subject, and the recording electrodes of the electrode system are configured to detect electrical activity of at least one of a muscular response or a nerve response to the delivered electrical pulse.

20. The electrode system of claim 1, wherein a surface area of each of the one or more stimulating electrodes is greater than a surface area of each of the recording electrodes.

21. The electrode system of claim 20, wherein the surface area of each of the one or more stimulating electrodes is approximately 1.5 times greater than the surface area of each of the recording electrodes.

22. The electrode system of claim 1, further comprising a temperature sensor for measuring a temperature of a subject to which the electrode system is applied, the temperature sensor being carried on the flexible substrate.

23. The electrode system of claim 1, further comprising a security IC chip configured to provide authentication between the electrode system and the monitoring system, the security IC chip being carried on the flexible substrate.

24. The electrode system of claim 1, wherein the electrodes of the electrode system consist only of one or more stimulating electrodes and recording electrodes carried on the flexible substrate and do not include a common ground electrode.

25. A method for manufacturing an electrode system, comprising:
providing a flexible substrate having a length axis and a width axis, wherein said length axis is substantially greater than said width axis, said flexible substrate comprising no more than three islands which comprise a first island, a first bridge that connects the first island to a second island and a second bridge that connects the second island to a third island;
providing a connector interface on the flexible substrate, the connector interface being configured to communicatively connect the electrode system with a monitoring system;
providing one or more stimulating electrodes on the first island of the flexible substrate, the one or more stimulating electrodes being configured to deliver an electrical pulse;
providing no more than one recording electrodes on the second island of the flexible substrate, the one recording electrodes configured to detect an electrical signal;
providing only one recording electrode on the third island of the flexible substrate, the one recording electrode configured to detect an electrical signal; and
providing a plurality of conductive traces on the flexible substrate, wherein a first one of the plurality of conductive traces routes across the first island, the first bridge, the second island, and the second bridge to electrically connect the one recording electrode carried on the third island with the connector interface, and wherein a second one of the plurality of conductive traces routes across the first island and the first bridge to electrically connect the one recording electrode carried on the second island with the connector interface, and wherein a third one or more of the plurality of conductive traces electrically connect the one or more stimulating electrodes carried on the first island with the connector interface, wherein each of the one or more stimulating electrodes has a rectangular-elongate shape with a length dimension that is at least two times greater than a width dimension and said length dimension is substantially perpendicular to the length axis of the flexible substrate.

26. The method of claim 25, wherein the length dimension is at least five times greater than the width dimension.

27. The method of claim 25, wherein each of the one or more stimulating electrodes has at least one rounded corner.

28. The method of claim 25, wherein each of the one or more stimulating electrodes has a maximum surface area less than or equal to 1.5 cm$^2$.

29. The method of claim 25, further comprising providing a dielectric layer on the flexible substrate, wherein the dielectric layer provides electrical insulation between any two of the plurality of conductive traces, the one or more stimulating electrodes and the recording electrodes.

30. The method of claim 25, further comprising providing a foam layer on the flexible substrate, wherein the foam layer defines a plurality of openings around each of the one or more stimulating electrodes and the recording electrodes.

31. The method of claim 30, further comprising providing a conductive adhesive arranged in at least one of the plurality of openings in the foam layer, the conductive adhesive capable of binding to a subject's skin.

32. The method of claim 30, further comprising providing a transfer adhesive layer that binds the foam layer and the flexible substrate.

33. The method of claim 25, wherein providing the plurality of conductive traces further comprises printing at least one of a conductive silver or silver-carbon ink on the flexible substrate.

34. The method of claim 25, wherein each of the one or more stimulating electrodes and the recording electrodes comprises a first layer carried on the flexible substrate and a second layer carried on the first layer, the first layer being formed from at least one of a conductive silver or silver-carbon ink and the second layer being formed from a conductive silver-silver chloride ink.

35. The method of claim 34, wherein providing one or more stimulating electrodes and recording electrodes further comprises printing the first layer formed from the at least one of a conductive silver or silver-carbon ink on the flexible substrate and printing the second layer formed from the conductive silver-silver chloride ink on the first layer.

36. The method of claim 35, wherein each of the plurality of conductive traces is connected to the first layer of at least one of the one or more stimulating electrodes and the recording electrodes.

37. The method of claim 25, wherein a surface area of each of the one or more stimulating electrodes is greater than a surface area of each of the recording electrodes.

38. The method of claim 37, wherein the surface area of each of the one or more stimulating electrodes is approximately 1.5 times greater than the surface area of each of the recording electrodes.

39. The method of claim 25, further comprising providing a temperature sensor for measuring a temperature of a subject to which the electrode system is applied on the flexible substrate.

40. The method of claim 25, further comprising providing a security IC chip configured to provide authentication between the electrode system and the monitoring system on the flexible substrate.

41. The method of claim 25, wherein the electrodes of the electrode system consist only of one or more stimulating electrodes and recording electrodes carried on the flexible substrate and do not include a common ground electrode.

42. A system for assessing muscle electrical activity in a subject, comprising:
    a motor nerve stimulator configured to generate an electrical pulse to stimulate a targeted motor nerve of the subject;
    a recording apparatus for recording electrical activity of a muscle innervated by the motor nerve; and
    an electrode system comprising:
        a flexible substrate having a length axis and a width axis, wherein said length axis is substantially greater than said width axis, said flexible substrate comprising no more than three islands, which comprise a first island, a first bridge that connects the first island to a second island and a second bridge that connects the second island to a third island;
        a connector interface carried on the flexible substrate and configured to communicatively connect the electrode system with the motor nerve stimulator and the recording apparatus;
        one or more stimulating electrodes carried on the first island of the flexible substrate and configured to deliver the generated electrical pulse to a motor nerve of the subject;
        no more than one recording electrodes carried on the second island of the flexible substrate and configured to detect a muscle electrical activity of a muscle innervated by the motor nerve;
        one recording electrode on the third island of the flexible substrate, the one recording electrode configured to detect an electrical signal; and
        a plurality of conductive traces carried on the flexible substrate, wherein a first one of the plurality of conductive traces route across the first island, the first bridge, the second island, and the second bridge to electrically connect the one recording electrode carried on the third island with the connector interface, and wherein a second one of the plurality of conductive traces route across the first island and the first bridge to electrically connect the one recording electrode carried on the second island with the connector interface, and wherein a third one or more of the plurality of conductive traces electrically connect the one or more stimulating electrodes carried on the first island with the connector interface, wherein each of the one or more stimulating electrodes has a rectangular-elongate shape with a length dimension that is at least two times greater than a width dimension and said length dimension is substantially perpendicular to the length axis of the flexible substrate.

43. The system of claim 42, wherein the electrodes of the electrode system consist only of one or more stimulating electrodes and recording electrodes carried on the flexible substrate and do not include a common ground electrode.

* * * * *